(12) United States Patent
Price

(10) Patent No.: US 7,365,860 B2
(45) Date of Patent: *Apr. 29, 2008

(54) SYSTEM CAPABLE OF DETERMINING APPLIED AND ANODIZED COATING THICKNESS OF A COATED-ANODIZED PRODUCT

(75) Inventor: Joseph K. Price, Nebo, NC (US)

(73) Assignee: Sensory Analytics, Greensboro, NC (US)

( * ) Notice: Subject to any disclaimer, the term of this patent is extended or adjusted under 35 U.S.C. 154(b) by 226 days.

This patent is subject to a terminal disclaimer.

(21) Appl. No.: 11/031,967

(22) Filed: Jan. 7, 2005

(65) Prior Publication Data

US 2005/0196522 A1 Sep. 8, 2005

Related U.S. Application Data

(60) Continuation-in-part of application No. 10/953,082, filed on Sep. 29, 2004, and a continuation-in-part of application No. 10/952,700, filed on Sep. 29, 2004, which is a division of application No. 10/748,704, filed on Dec. 30, 2003, now Pat. No. 7,128,985, which is a division of application No. 09/742,595, filed on Dec. 21, 2000, now Pat. No. 6,674,533.

(51) Int. Cl.
*G01B 11/02* (2006.01)

(52) U.S. Cl. ..................... 356/503; 356/479; 356/482; 356/497; 356/504

(58) Field of Classification Search ................ 356/479, 356/482, 497, 503, 504
See application file for complete search history.

(56) References Cited

U.S. PATENT DOCUMENTS

| 3,328,774 | A | 6/1967 | Louvel |
| 3,959,091 | A | 5/1976 | Moji et al. |
| 4,014,758 | A | 3/1977 | Kawai et al. |
| 4,068,156 | A | 1/1978 | Johnson et al. |
| 4,251,330 | A | 2/1981 | Sheasby et al. |

(Continued)

FOREIGN PATENT DOCUMENTS

| EP | 0 601 580 A1 | 6/1994 |
| EP | 0 631 106 | 12/1994 |
| EP | 0 639 753 | 2/1995 |

OTHER PUBLICATIONS

PCT Search Report Issued by the European Patent Office for PCT/US2005/047585 mailed Jul. 25, 2006.

*Primary Examiner*—Archene Turner
(74) *Attorney, Agent, or Firm*—Kilpatrick Stockton LLP

(57) ABSTRACT

A system for forming an anodized coating on at least a portion of a substrate thereby creating an anodized substrate is disclosed. The system includes a bath, a coating thickness monitor, at least one probe and at least one controller. The coating thickness monitor includes at least one radiation source directed at at least a portion of the anodized substrate; at least one probe for capturing at least a portion of the radiation reflected and refracted by the anodized coating on the anodized substrate, the captured radiation being at least a portion of the radiation directed the anodized substrate from the radiation source; and at least one detector in communication with the at least one probe, the at least one detector capable of processing the captured radiation to allow a determination of at least the thickness.

19 Claims, 12 Drawing Sheets

U.S. PATENT DOCUMENTS

| | | |
|---|---|---|
| 4,344,127 A | 8/1982 | McDaniel et al. |
| 4,352,620 A | 10/1982 | Inaba et al. |
| 4,396,976 A | 8/1983 | Hyatt |
| 4,417,845 A | 11/1983 | Burton |
| 4,478,689 A | 10/1984 | Loch |
| 4,537,664 A | 8/1985 | Novacek |
| 4,555,767 A | 11/1985 | Case et al. |
| 4,645,349 A | 2/1987 | Tabata |
| 4,646,223 A | 2/1987 | Sekiguchi |
| 4,748,329 A | 5/1988 | Cielo et al. |
| 4,756,619 A | 7/1988 | Gerlinger et al. |
| 4,777,603 A | 10/1988 | Woodman et al. |
| 4,802,763 A | 2/1989 | Gerlinger et al. |
| 4,835,710 A | 5/1989 | Schnelle et al. |
| 4,872,755 A | 10/1989 | Kuchel |
| 4,894,127 A | 1/1990 | Wong et al. |
| 4,916,600 A | 4/1990 | Ropelato |
| 4,919,535 A | 4/1990 | Hohberg et al. |
| 4,979,093 A | 12/1990 | Laine et al. |
| 4,984,894 A | 1/1991 | Kondo |
| 5,042,949 A | 8/1991 | Greenberg et al. |
| 5,289,266 A | 2/1994 | Shih et al. |
| 5,291,269 A | 3/1994 | Ledger |
| 5,337,150 A | 8/1994 | Mumola |
| 5,351,200 A | 9/1994 | Impink, Jr. |
| 5,365,340 A | 11/1994 | Ledger |
| 5,452,953 A | 9/1995 | Ledger |
| 5,579,218 A | 11/1996 | Ehlig et al. |
| 5,689,415 A | 11/1997 | Calotychos et al. |
| 5,693,208 A | 12/1997 | Paulet |
| 5,726,912 A | 3/1998 | Krall, Jr. et al. |
| 5,851,373 A | 12/1998 | Kubota et al. |
| 5,866,917 A | 2/1999 | Suzuki et al. |
| 5,867,385 A | 2/1999 | Brown et al. |
| 5,872,892 A | 2/1999 | Brown et al. |
| 5,923,429 A | 7/1999 | Takeuchi et al. |
| 5,980,078 A | 11/1999 | Krivoshein et al. |
| 5,999,262 A | 12/1999 | Dobschal et al. |
| 6,038,027 A * | 3/2000 | Marcus et al. ............ 356/503 |
| 6,052,191 A | 4/2000 | Brayden, Jr. et al. |
| 6,128,081 A | 10/2000 | White et al. |
| 6,278,809 B1 | 8/2001 | Johnson et al. |
| 2002/0112967 A1 | 8/2002 | Price |
| 2004/0231993 A1 | 11/2004 | Price |

* cited by examiner

FIG. 12

SYSTEM CAPABLE OF DETERMINING APPLIED AND ANODIZED COATING THICKNESS OF A COATED-ANODIZED PRODUCT

The present application is a continuation-in-part of U.S. application Ser. No. 10/952,700, filed on Sep. 29, 2004, and U.S. application Ser. No. 10/953,082, filed on Sep. 29, 2004, which are divisional applications of U.S. application Ser. No. 10/748,704, filed on Dec. 30, 2003 now U.S. Pat. No. 7,128,985, which is a divisional application of U.S. application Ser. No. 09/742,595, filed on Dec. 21, 2000, that was issued on Jan. 6, 2004 as U.S. Pat. No. 6,674,533.

BACKGROUND OF THE INVENTION (1) Field of the Invention

The present invention relates generally to a system including a coating thickness monitor and, more particularly, to a system capable of determining applied and anodized coating thickness on a substrate as each is being formed as well as determining applied and anodized coating thickness subsequent to their formation.

(2) Description of the Prior Art

The coating of metallic substrates such as aluminum and zinc using anodizing is known. Anodizing is done for practical and aesthetic reasons. From a practical perspective, the creation of a coating on the surface of a metallic substrate contributes to an anodized product's wear resistance, corrosion resistance, and oxidation resistance. From an aesthetic perspective, the creation of a coating including a dye for coloration on the surface of a metallic substrate contributes to an anodized product's consumer appeal. In both industrial and aesthetic applications, it is desirable to control the thickness of the anodized coating as well as the consistency over a given surface area.

Commonly, coating thickness is determined by destructive methods. For example, in a batch anodizing system, control coupons made of the same material as a product to be anodized are included in the anodizing bath. At intermediate times during the anodizing process a control coupon is removed from the bath and destroyed in a manner that permits determining the coating thickness.

One destructive method includes mounting a control coupon in a Bakelite cross-section, polishing the mounted coupon to a mirror finish and examining the polished cross-section using an optical microscope to determine the coating thickness. A second destructive method includes cutting or breaking a control coupon to expose a cross-section and examining the cross-section using scanning electron microscopy to determine the coating thickness. These destructive methods are cumbersome in production.

Both destructive methods delay production because of the time taken to remove and prepare control coupons for determining coating thickness. During the delay, the bath is idle. An alternative is to remove the product from the anodizing bath while determining coating thickness and replace it with a second product and corresponding control coupons. In this case, storage area for the product removed from the bath during a coating thickness determination would be required at the production site.

Although using an anodizing bath alternatively with multiple products provides a solution to production delay, coating flaws can be introduced by bath chemistry changes and surface contagion during storage. That is, the different bath chemistry when the product is reintroduced after the coating thickness determination for further anodizing may create a distinct mismatched interface with the original coating.

During storage, the original coating on the product may also be damaged during removal from and replacement into the anodizing bath. Particulate matter such as dust also may attach to the surface to introduce further interfacial flaws between the original coating and the further coating.

The above destructive methods have another serious flaw, namely, that the determined coating thickness is that of a control coupon and not of the product. Thus, the coating thickness of the product is only an estimate and the coating thickness consistency over the entire surface of the product is unknown.

Thus, there remains a need for a new and improved system that includes a coating thickness monitor that non-destructively determines the coating thickness on a product, while at the same time, has the ability to control the anodizing system. There also remains a need for a coating thickness monitor that nondestructively determines the coating thickness on an coated-anodized product.

SUMMARY OF THE INVENTION

The present invention is directed to a system for forming an anodized coating on at least a portion of a substrate thereby creating an anodized substrate. The anodizing system includes a bath, a coating thickness monitor, at least one probe, and at least one controller. The substrate is placed into the bath to facilitate the formation of the anodized coating on at least a portion of the substrate, thereby creating the anodized substrate. The coating thickness monitor measures the thickness of at least a portion of the anodized coating formed on the substrate in the bath. The coating thickness monitor includes at least one radiation source directed at at least a portion of the anodized substrate; at least one probe for capturing at least a portion of the radiation reflected and refracted by the anodized coating on the anodized substrate, the captured radiation being at least a portion of the radiation directed the anodized substrate from the radiation source; at least one detector in communication with the at least one probe, the at least one detector capable of processing the captured radiation to allow a determination of at least the thickness of the anodized coating on the substrate; and at least one guide system capable of transmitting the captured radiation from the at least one probe to the at least one detector. The at least one controller is in communication with the coating thickness monitor and the bath.

In one embodiment, the at least one controller regulates a relative movement of the probe and the anodized substrate. In another embodiment, the at least one controller regulates at least one process parameter of the bath. Preferably, the regulate process parameter includes at least one of bath chemistry, bath temperature, anodizing voltage, anodizing current and anodizing time. In another embodiment, the at least one controller regulates a process endpoint.

The guide system for the captured radiation may be an optical guide, preferably, an optical fiber, more preferably, a plurality of optical fibers.

An additional guide system may be added to the coating thickness monitor. This additional guide system is capable of transmitting at least a portion of the radiation from the at least one radiation source to direct at least a portion of the radiation at at least a portion of the anodized substrate. The additional guide system may be an additional optical guide, preferably an optical fiber, more preferably, a plurality of optical fibers.

Also, a supplementary guide system may be added to the coating thickness monitor. The supplementary guide system is capable of at least one of: (1) transmitting additional captured radiation from the at least one probe to the at least one detector; (2) transmitting at least a portion of the radiation from at least one additional radiation source to direct at least a portion of the additional radiation at at least a portion of the anodized substrate; and (3) transmitting at least a portion of the additional radiation from at least one additional radiation source to direct the at least a portion of the additional radiation at at least a portion of the anodized substrate and transmitting the additional captured radiation from the at least one probe to the at least one detector, the additional captured radiation being at least a portion of the additional radiation directed at the anodized substrate from the at least one additional radiation source. The supplementary guide may be an additional optical guide, preferably an optical fiber, more preferably a plurality of optical fibers.

The guide system and the supplementary guide system are selected to be capable of transmitting a broad spectral range of captured radiation from the at least one probe to the at least one detector.

In one embodiment, the at least one radiation source is polychromatic and includes at least one of ultraviolet radiation, visible radiation, and infrared radiation. In another embodiment, the at least one source radiation is monochromatic. An additional radiation source may also be included with the coating thickness monitor. In one embodiment, the additional radiation is polychromatic and includes at least one of ultraviolet radiation, visible radiation, and infrared radiation. In another embodiment, the additional radiation is monochromatic. In a preferred embodiment relating to at least one radiation source and an additional radiation source, a spectral range of the at least one radiation source and a spectral range of the additional radiation source partially overlap. The partial overlap increases at least one of a signal to noise ratio for the captured radiation and a total spectral range of captured radiation. Preferably, one of the at least one radiation source and the additional radiation source is visible radiation and the other of the at least radiation source and the additional radiation source is infrared radiation.

The at least one probe may further include a collimator that facilities a depth of field of a sufficient value to measure the anodized coating thickness. In one embodiment, the at least one probe is external to the bath. In an alternative embodiment, the at least one probe is within the bath.

The at least one detector may include an interferometer. The processing of the captured radiation to determine the coating thickness by the coating thickness monitor includes at least one of using a color, using an interference pattern, using an amount of absorbed radiation, using an intensities ratio of a minimum reflected radiation wavelength and a maximum reflected radiation wavelength, and using a Fast Fourier Transformation (FFT) of the captured radiation. Preferably, the processing of the captured radiation to determine the coating thickness by the coating thickness monitor includes using a Fast Fourier Transformation (FFT) of the captured radiation.

Accordingly, one aspect of the present invention is to provide an anodizing system for forming an anodized coating on at least a portion of a substrate thereby creating an anodized substrate. The anodizing system includes a bath and a coating thickness monitor. The substrate is placed into the bath to facilitate the formation of the anodized coating on at least a portion of the substrate thereby creating the anodized substrate. The coating thickness monitor measures the thickness of at least a portion of the anodized coating on the substrate formed in the bath. The coating thickness monitor includes at least one radiation source directed at at least a portion of the anodized substrate, at least one probe for capturing at least a portion of the radiation reflected and refracted by the anodized coating on the anodized substrate, the captured radiation being at least a portion of the radiation directed to the anodized substrate from the radiation source, and at least one detector in communication with the at least one probe, the at least one detector capable of processing the captured radiation to allow a determination of at least the thickness of the anodized coating on the substrate.

Another aspect of the present invention is to provide a coating thickness monitor for measuring the thickness of at least a portion of an anodized coating on at least a portion of a substrate. The anodizing system has a bath into which the substrate is placed to facilitate the formation of the anodized coating on the substrate thereby creating the anodized substrate. The coating thickness monitor includes at least one radiation source directed at at least a portion of the anodized substrate; at least one probe for capturing at least a portion of the radiation reflected and refracted by the anodized coating on the anodized substrate, the captured radiation being at least a portion of the radiation directed the anodized substrate from the radiation source; at least one detector in communication with the at least one probe, the at least one detector capable of processing the captured radiation to allow a determination of at least the thickness of the anodized coating on the substrate, and a guide system capable of transmitting the captured radiation from the at least one probe to the at least one detector.

Still another aspect of the present invention is to provide an anodizing system for forming an anodized coating on at least a portion of a substrate thereby creating an anodized substrate. The anodizing system includes a bath, a coating thickness monitor, at least one probe and at least one controller. The substrate is placed into the bath to facilitate the formation of the anodized coating on at least a portion of the substrate thereby creating the anodized substrate. The coating thickness monitor measures the thickness of at least a portion of the anodized coating formed on the substrate in the bath. The coating thickness monitor includes at least one radiation source directed at at least a portion of the anodized substrate, at least one probe for capturing at least a portion of the radiation reflected and refracted by the anodized coating on the anodized substrate, the captured radiation being at least a portion of the radiation directed the anodized substrate from the radiation source, at least one detector in communication with the at least one probe, the at least one detector capable of processing the captured radiation to allow a determination of at least the thickness of the anodized coating on the substrate, and at least one guide system capable of transmitting the captured radiation from the at least one probe to the at least one detector. The at least one controller is in communication with the coating thickness monitor and the bath.

These and other aspects of the present invention will become apparent to those skilled in the art after a reading of the following description of the preferred embodiments, when considered with the drawings.

BRIEF DESCRIPTION OF THE DRAWINGS

Figure 12:
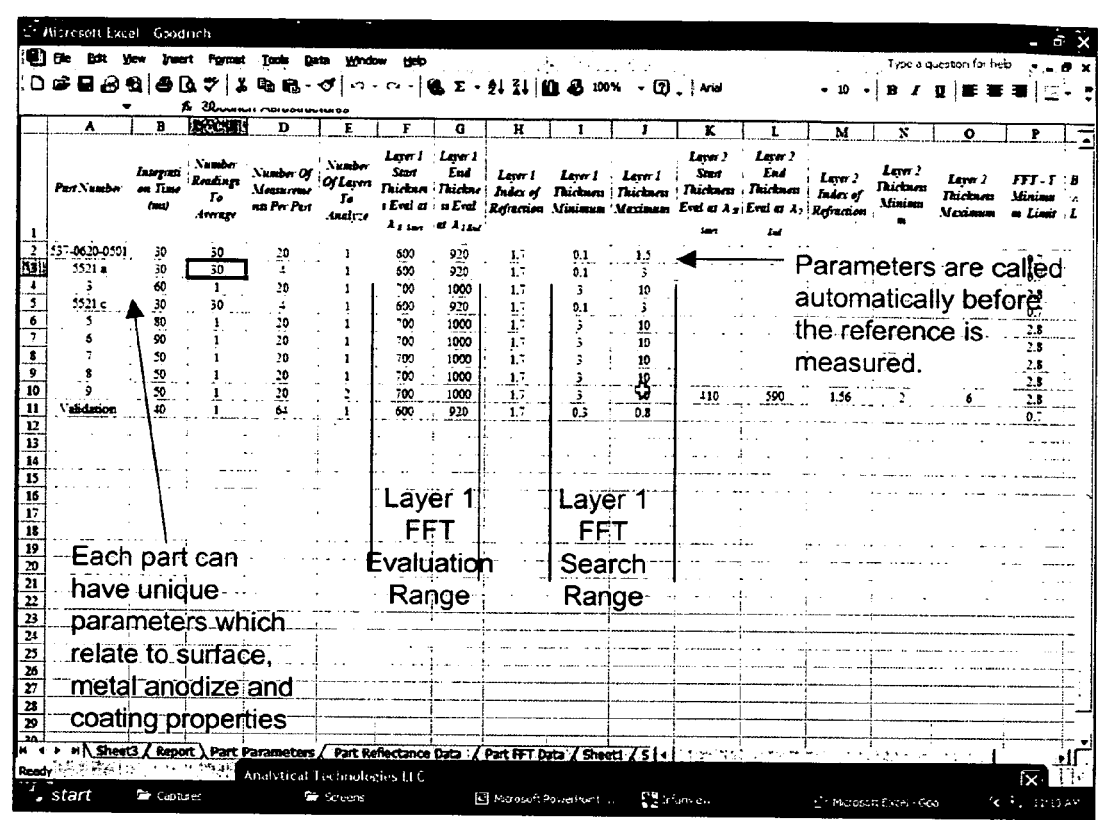

FIG. 12 depicts a optIcons® parametric data repository which is used to configure multi-layer analysis.

DESCRIPTION OF THE PREFERRED EMBODIMENTS

Figure 1:
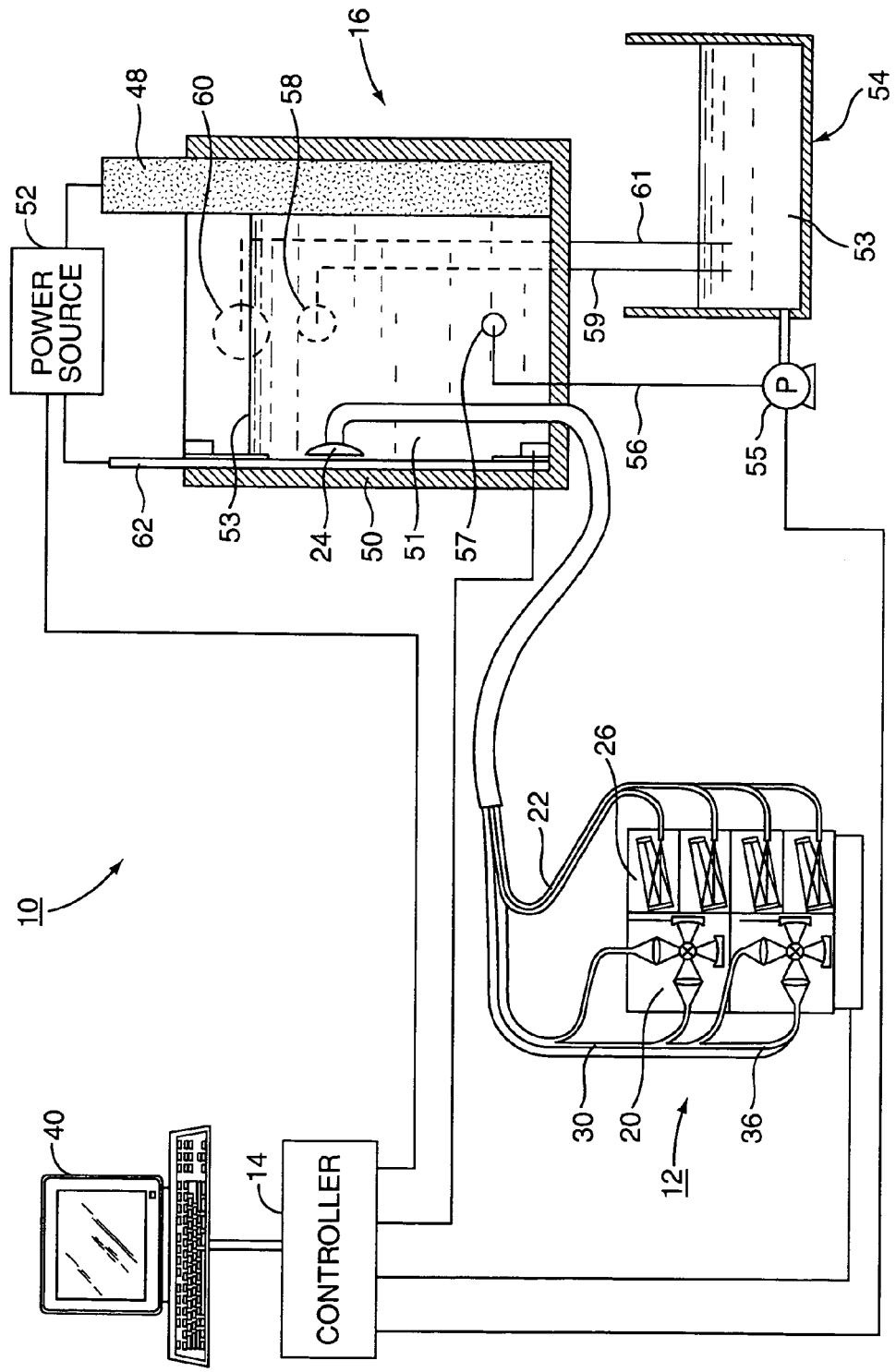
FIG. 1 depicts an anodizing system including a coating thickness monitor according to an aspect of the present invention.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, an anodizing system 10 includes a bath 16 and a coating thickness monitor 12. A substrate 62 is submersed into the bath 16 for coating. The anodizing system 10 may further include a controller 14.

The coating thickness monitor 12 includes at least one radiation source 20, a probe 24 for capturing radiation reflected and/or refracted from the substrate 62 and through the coating 72, and a detector 26 that is coupled to the probe 24. The detector 26 deconvolutes the spectrum of the captured reflected and/or refracted radiation to determine the coating thickness.

Figure 2:
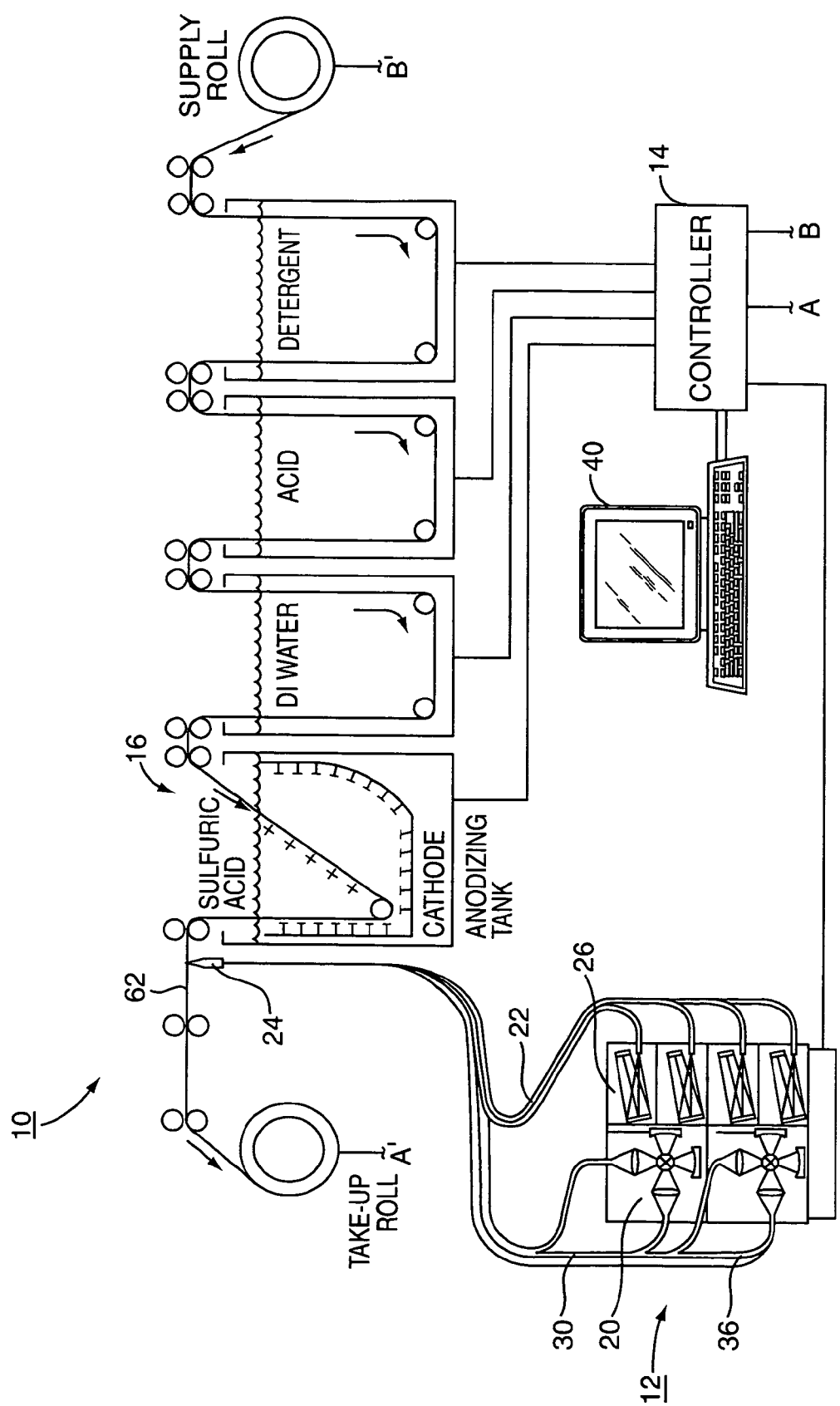
FIG. 2 depicts an alternative anodizing system including a coating thickness monitor according to an aspect of the present invention.
Figure 3:
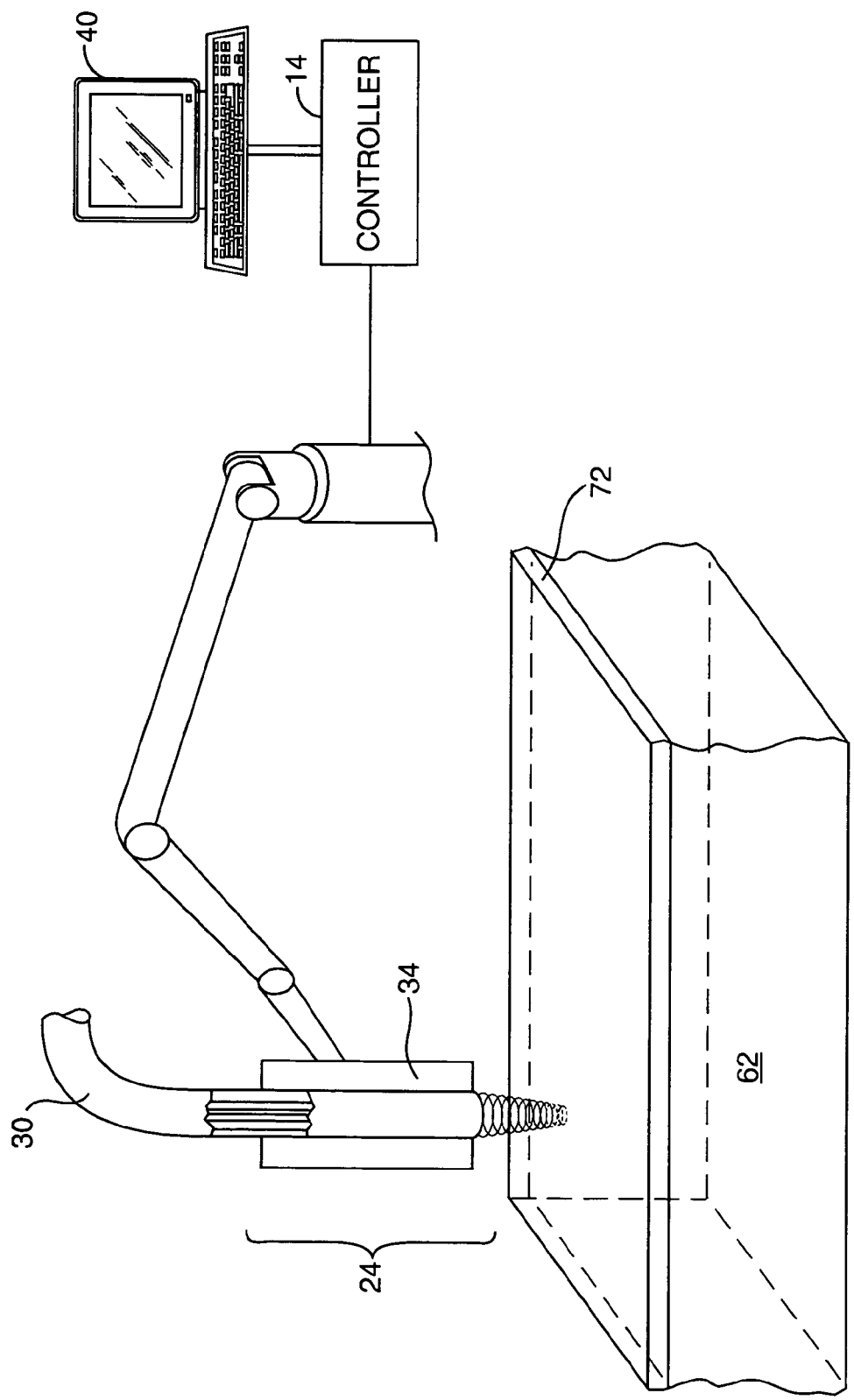
FIG. 3 depicts a probe of a coating thickness monitor adjacent to a substrate suitable useable with an anodizing system as depicted in FIGS. 1 and 2 according to an aspect of the present invention.
Figure 4:
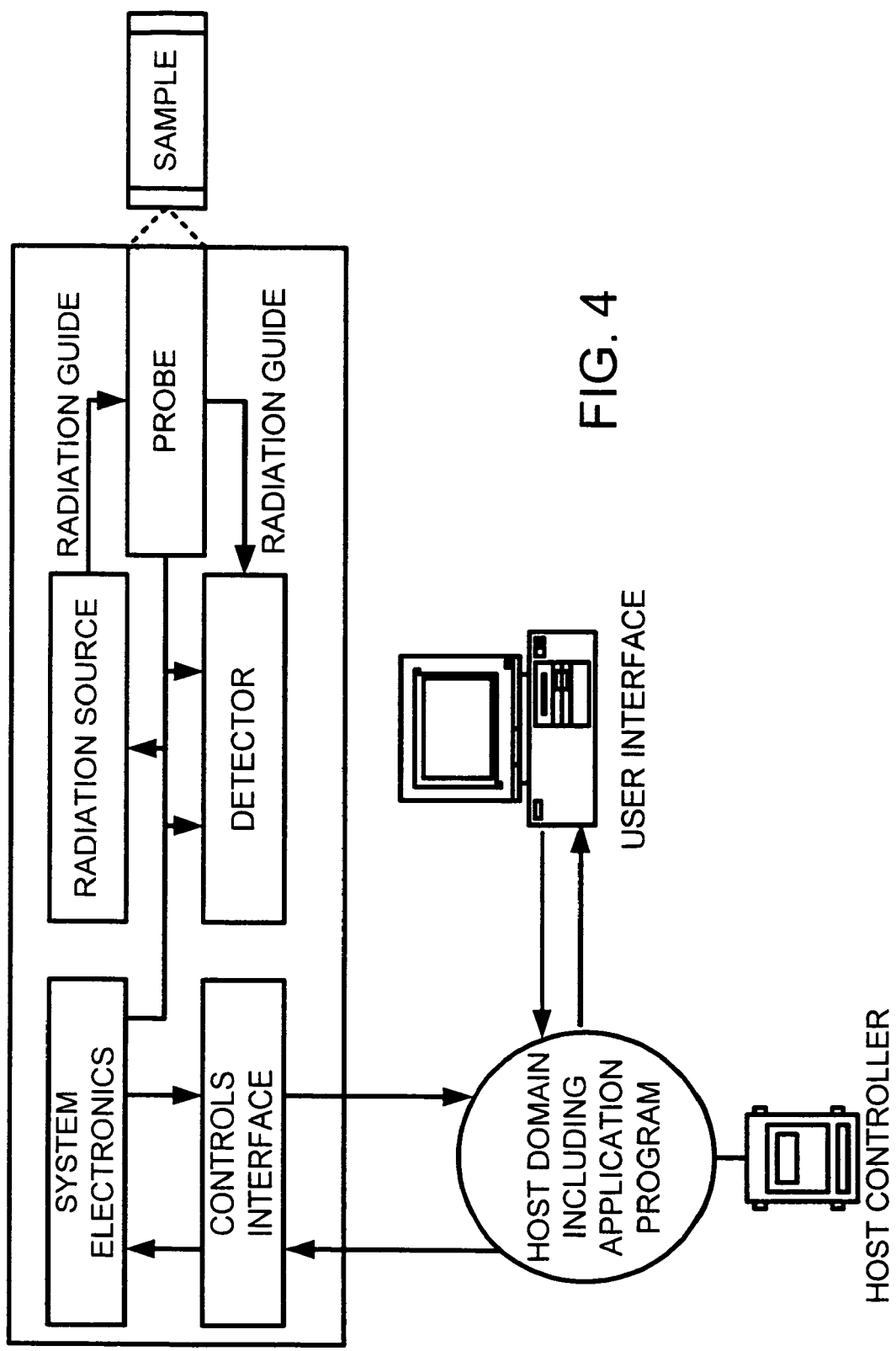
FIG. 4 depicts a block diagram of the coating thickness monitor useable with an anodizing system as depicted in FIGS. 1 and 2 according to an aspect of the present invention.

In FIG. 1, the probe 24 is shown to be within the bath 16. However, Applicant contemplates that the probe 24 may be outside of bath 16, as shown in FIGS. 2 & 3. In such an arrangement, the substrate 62 may be removed from the bath 16 at intermediate times and probe 24 moved along the substrate 62 surface without contacting the surface to determine the coating thickness over the surface area of the substrate 62. It is advantageous for probe 24 to move over the surface of the substrate 62 without contacting the surface to not be altered or damaged coating 72 during the thickness determination.

The bath 16 includes an electrode 48, a treatment bath 50, a power source 52, which may be a direct current power source. Also, bath 16 may include a reservoir 54 for storing an electrolyte 53 and a pump 55 for circulating the electrolyte 53. The electrolyte 53 is supplied to the treatment bath 50 through a feed pipe 56 and an electrolyte inlet 57 in the treatment bath 16. A portion of the electrolyte 53 may be returned to the reservoir 54 through an electrolyte outlet 58 and a return pipe 59. Another portion of the electrolyte 53 may be returned to the reservoir 54 through an overflow port 60 and an overflow pipe 61. The electrolyte 53 in the reservoir 54 is controlled by a predetermined temperature and by a means of controller 14.

When power source 52 is a direct current (DC) power source, the electrode 48 in electrolyte bath 51 is connected to the plus terminal of the DC power source 52. Substrate 62 is connected to the minus terminal of the DC power source 52. When electric current is supplied from the DC power source 52 under these conditions, it flows through the electrode 48 and the electrolyte 53. The electrical current then flows into the substrate 62 through an anodizing film 72. The electric current then flows back to the DC power supply 52. More details concerning baths and anodizing systems are discussed in, for example, U.S. Pat. Nos. 5,851,373; 5,693,208; 4,894,127; 4,537,664; 4,478,689; 4,251,330; 4,014,758; and 3,959,091, the entire disclosure of each being incorporated by reference herein.

Turning now to FIG. 2, there is shown a continuous anodizing process, the view being generally diagrammatic. This anodizing system 10 likewise includes a bath 16 and a coating thickness monitor 12. A probe 24 captures the reflected and/or refracted radiation from a substrate 62, which may include a foil, sheet, or wire product. In this anodizing system 10, substrate 62 is provided on a supply roll (roll depicted on the right of FIG. 2). After anodizing, the substrate 62, including a coating 72, is removed on a take-up roll (roll depicted on the left of FIG. 2). Prior to anodizing, the surfaces of substrate 62 may be cleaned by immersing the substrate 62 in a detergent (first tank depicted to the left of the supply roll in FIG. 2) to remove foreign materials such as grease and dust that interfere with coating adhesion. A further cleaning of the substrate 62 may include a pickling operation ([second tank depicted to the left of the supply roll in FIG. 2] the process of removing scale or other surface compounds by immersion in a suitable aggressive liquid; sometimes electrochemically assisted to clean the surface) followed by an acid removal step (third tank depicted to the left of the supply roll in FIG. 2) that may involve immersing the substrate 62 in deionized water. The continuous anodizing of the substrate 62 may then follow.

After anodizing, a probe 24 is used for measuring the thickness of the coating 72. In an aspect of the present invention, a probe 24 remains stationary as an anodized substrate 62 moves by, thereby measuring a thickness along a length of the product. In another aspect of the present invention, a probe 24 also moves substantially perpendicular to the direction of the movement of an anodized substrate 62 thereby measuring a thickness along an area of the substrate. In this manner, a coating thickness distribution over the surface of a product such as a sheet, coil or foil may be determined. As best seen in FIG. 3, a robotic arm may be used to move a probe 24 across a substrate 62 having a coating 72 to determine the coating thickness at a select point, a select region or even over the entire surface of a product. More details concerning motion control and robotics are discussed in, for example, U.S. Pat. Nos. 5,872,892; 4,979,093; 4,835,710; 4,417,845; 4,352,620; and 4,068,156, the entire disclosure of each being incorporated by reference herein.

As best seen in FIGS. 1 and 2, a coating thickness monitor 12 includes at least one radiation source 20, a probe 24 for capturing the reflected and/or refracted radiation, and a detector 26 for measuring or deconvoluting the spectrum of the reflected and/or refracted radiation.

A radiation source 20 may be polychromatic, for example, ultraviolet (UV), visible, infrared (IR), or monochromatic. A radiation source 20 that is polychromatic may be a subset of any of UV (having wavelengths in the range of about 4 to about 400 nanometers), visible (having radiation wavelengths to which the organs of sight react, ranging from about 400 to about 700 nanometers), and IR (having wavelengths between 750 nanometers and 1 millimeter). Examples of such subsets include vacuum ultraviolet radiation (UV radiation having wavelengths less than about 200 nanometers; so-called because at shorter wavelengths the radiation is strongly absorbed by most gases), far-ultraviolet radiation (the short-wavelength region of the UV range: about 50 to about 200 nanometers), near-ultraviolet radiation (ultraviolet radiation having wavelengths in the range of about 300 to 400 nanometers), far-infrared radiation (long-wavelength region of the infrared range: about 50 to about 1000 micrometers) and near-infrared radiation (radiation having wavelengths in the range of about 0.75 to about 2.5 micrometers). Alternatively, a radiation source 20 may be monochromatic.

In an embodiment, a coating thickness monitor 12 includes an additional radiation source 28. The radiation source 20 and additional radiation source 28 may be any one of polychromatic and monochromatic and are selected to compliment each other to improve, for example, the intensity and breadth of reflected radiation available for determining the thickness of a coating 72 on a substrate 62. Typically, a single radiation source has an intensity that is greatest in a central range but decreasing on either end. By complimenting this with an additional source of radiation, there can be an overlap of the decreasing intensities to remove them. In this way, several advantages may be realized. For example, there may be an increase of signal to noise ratio with respect to the reflected radiation. Also, there may be an increase in the range of reflected radiation that can be captured. In this way, the other aspects of a coating's properties may be determined.

As seen in FIGS. 1 and 2, the probe 24, for capturing the reflected and/or refracted radiation, includes a guide for delivering the radiation back to the detector 26. As shown in FIG. 3, the probe 24, for capturing and directing the reflected and/or refracted radiation back to the detector 26, may include a collimator 34. The collimator 34 may be used to direct the captured reflected radiation into the coupler that directs the radiation to the detector 26. As mentioned earlier, the probe 24 may either be external to the bath 16 or within the bath.

The detector 26 is the type that demodulates the reflected spectrum once it is received. Examples of equipment that might be used with this are included in, for example, U.S. Pat. Nos. 6,052,191; 5,999,262; 5,289,266; 4,748,329; 4,756,619; 4,802,763; 4,872,755; and 4,919,535, the entire disclosure of each being incorporated by reference herein. Part of determining the coating thickness is through demodulating the reflected spectrum. Various techniques are known for measuring this including color interference method, absorption method, ratio of the intensity of the maximum wavelength to the intensity of the minimum wavelength and the fast Fourier transform (FFT) method (e.g., the processing of a signal generated by waves striking a detector, whereby the signal is transformed into a digital time series for spectrum analysis). More details concerning single and multiple coating thickness determination are discussed in, for example, U.S. Pat. Nos. 6,128,081; 6,052,191; 5,452,953, 5,365,340; 5,337,150; 5,291,269; 5,042,949; 4,984,894; 4,645,349; 4,555,767; and 4,014,758, the entire disclosure of each being incorporated by reference herein.

In an embodiment, a coating thickness detector 26 includes a guide system 30. The guide system 30 acts as a coupler to direct the reflected radiation from the probe 24 to the detector 26. The guide system 30 may also act to provide the source radiation to the surface of substrate 62 through the probe 24. Alternatively, a radiation source may be integral to probe 24 to provide the source radiation to capture the reflected radiation from the substrate 62, having a coating 72.

In a preferred embodiment, guide system 30 is a fiber optic guide that includes a plurality of fibers arranged in a manner to capture the radiation optimally, having a composition that transmits the reflected radiation without attenuation. The guide system 30 may include multiple components. In a more preferred embodiment, the guide system 30 is coupled with the radiation source 20 to direct radiation to the surface of the substrate 62, as well as being coupled to the detector 26 to direct the reflected and/or refracted radiation to the detector for analysis. Guide system 30 may include multiple sets of fibers when the coating thickness monitor includes multiple radiation sources and multiple detectors. The configuration and composition of optical fiber bundles are selected to optimally transmit the radiation interest.

As seen in FIGS. 1 and 2, the anodizing system 10 may include a controller 14 that may include, for example, a computer 40. The anodizing system 10 may operate without the computer 40 or an intermediate box to communicate with the controller 14.

Referring back to FIG. 1, and the controller system 14, the in situ and real time measurement of the coating thickness development by having the probe 24 within the bath 16 may be beneficial. In one aspect of the present invention, the benefits realized by this are the regulation of the anodizing process by controlling the process parameters, for example, the bath chemistry which can be done by controlling pump 55 to bring additional electrolyte to the bath 16 from the reservoir 54. Also, the anodizing voltage provided by power supply 52 can be adjusted during the process to give the desired coating 72; likewise, the anodizing current, the bath temperature, as well as the anodizing time, may be controlled. More details concerning controllers that may be used in anodizing system 10 are discussed in, for example, U.S.

Pat. Nos. 5,980,078; 5,726,912; 5,689,415; 5,579,218; 5,351,200; 4,916,600; 4,646,223; 4,344,127; and 4,396,976, the entire disclosure of each being incorporated by reference herein.

In this regard, with reference to FIG. 1, a controller 14 in combination with the coating thickness monitor 12 may be used as an endpoint determiner in a batch anodizing system. During anodizing, the process parameters may be controlled while allowing an operator to know, in real time, the thickness of the coating 72. At a time that the coating 72 grows to a desired thickness on the substrate 62, the process shuts down. Clearly, this ability to know the coating thickness as it grows is advantageous over any method where substrate 62 is removed from the bath 16, its coating thickness determined and then replaced into the bath.

Figure 5:
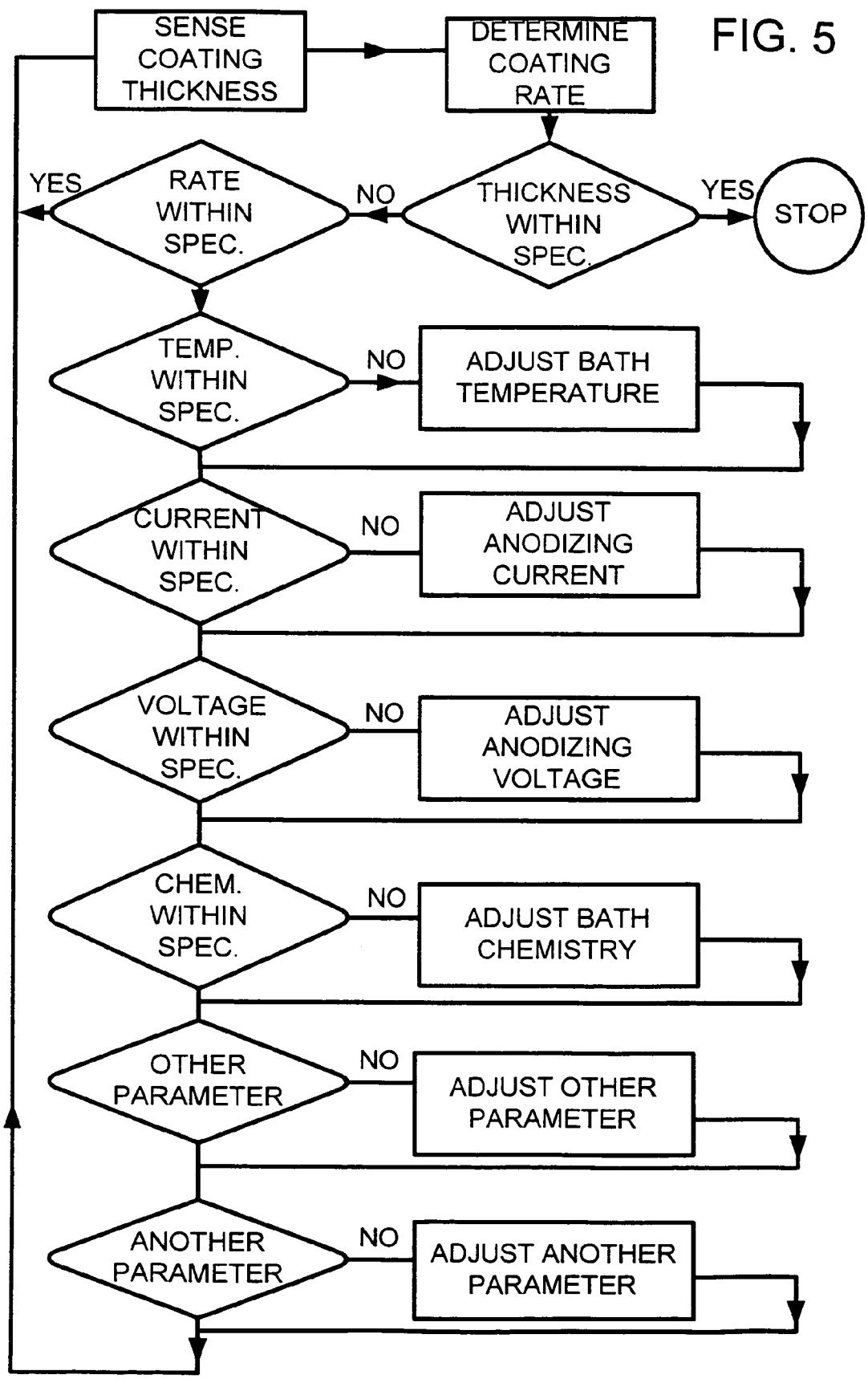
FIG. 5 depicts a controller block diagram useable with an anodizing system as depicted in FIG. 1 according to an aspect of the present invention.

FIG. 5 depicts a controller block diagram useable with an anodizing system as depicted in FIG. 1. Although the tasks of FIG. 5 are shown as being performed in a serial manner, Applicant contemplates that the tasks may be performed in parallel and any combination of serial and parallel that accomplishes the purpose, intent and/or function of the present invention. Again referring to FIG. 5, a probe is used to determine the coating thickness at any instant of time. Subsequently, a coating rate may be calculated. Then it is determined if the coating thickness has attained the desired value (e.g., whether the thickness is within the desired specification). When the desired coating thickness value has been attained, the coating process is stopped; otherwise, it is determined if the coating rate is at the desired value (e.g., whether the coating rate is within the desired specification). When a coating rate is not the desired coating rate, the value of other process parameters is measured and compared to a desired value for each (e.g., whether a process parameter is within a desired specification). If any process parameter, such as, bath temperature, anodizing current, anodizing voltage, bath chemistry, . . . etc., is not at its desired value, the process parameter is adjusted, then the query, compare, and adjust cycle is rerun until the desired coating thickness is attained.

A benefit of the present invention is the ability to produce an anodized substrate having a better quality and consistency from batch-to-batch, both linear and areal, over the length and surface better than an anodized substrate made without a coating thickness monitor of the present invention, and preferably, communicating with a controller. Table 1 includes a comparison of the quality (e.g., conformity to design specifications), consistency (e.g., the uniformity of a manufactured anodized substrate from batch-to-batch), and quality x consistency for a batch anodizing system of the present invention and the prior art. Although an anodized substrate of the prior art may be satisfactory with respect to both quality and consistency, an anodized substrate according to the present invention possesses better quality and excellent consistency.

As seen in FIG. 2, the interface of the coating thickness monitor 12 and the controller 14 in continuous coating operation may provide numerous advantages. In this system, the real time coating thickness determination may be fed back to control the processing parameters such as bath chemistry, voltage, current and temperature. Likewise, the take up speed may be controlled. In this way, a substrate 62 having an anodized coating that has a more consistent coating thickness per unit length or unit area may be manufactured. That is, by monitoring the coating in real time and adjusting all the process parameters, a more uniform coating can be realized.

Figure 6:
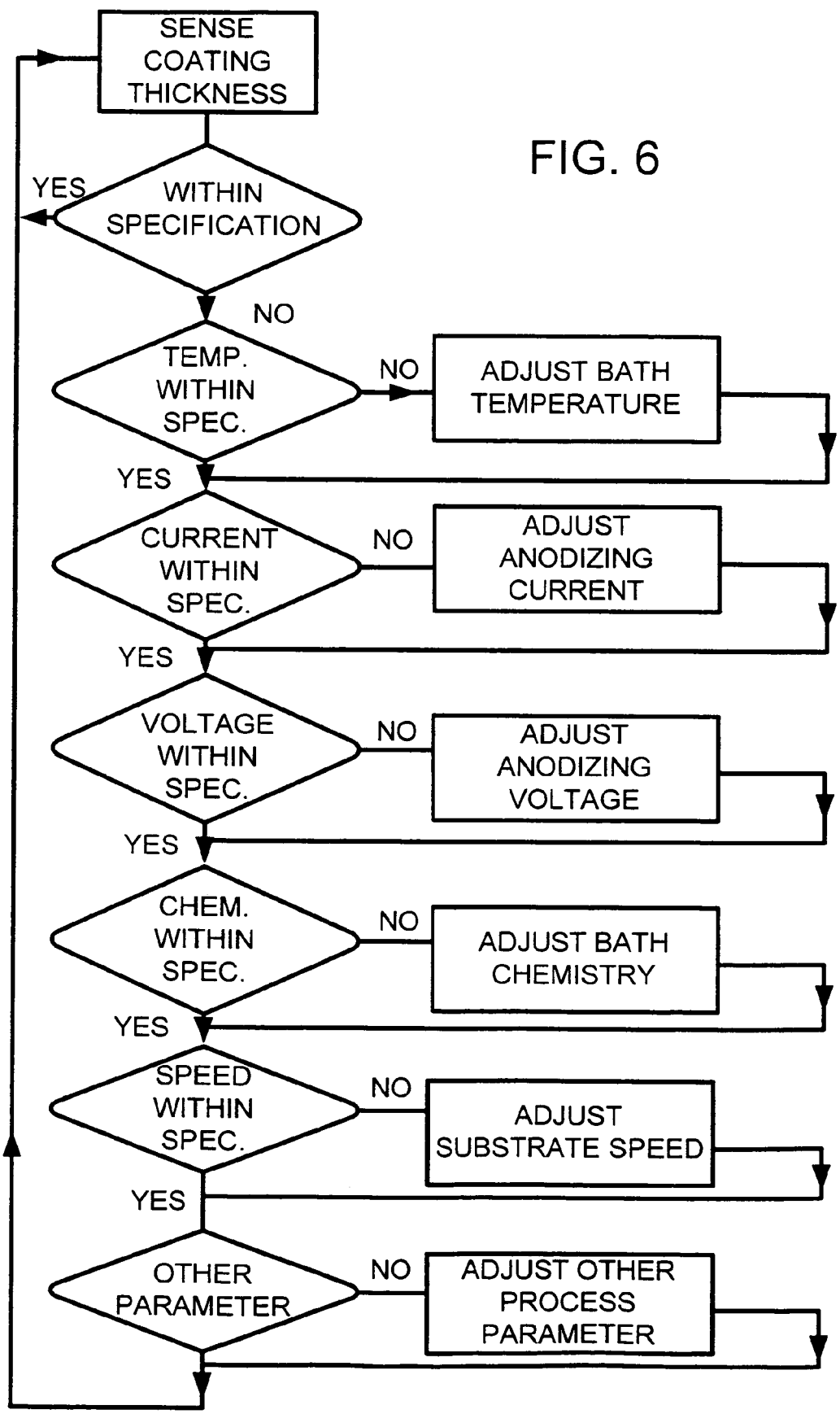
FIG. 6 depicts a controller block diagram useable with an anodizing system as depicted in FIG. 2 according to an aspect of the present invention.

FIG. 6 depicts a controller block diagram useable with an anodizing system, as depicted in FIG. 2. Although the tasks of FIG. 6 are shown as being performed in a serial manner, Applicant contemplates that the tasks may be performed in parallel and any combination of serial and parallel that accomplishes the purpose, intent and/or function of the present invention. Again referring to FIG. 6, a probe is used to determine the coating thickness at any instant of time. Subsequently, it is determined if the coating thickness has attained the desired value (e.g., whether the thickness is within the desired specification). When the desired coating thickness value has been attained, the coating process continues; otherwise, it is determined if the value of other process parameters is measured and compared to the desired value for each (e.g., whether a process parameter is within a desired specification). If any process parameters, such as, bath temperature, anodizing current, anodizing voltage, bath chemistry, roll speed, . . . etc., is not at a desired value, the process parameter is adjusted. Then the query, compare, and adjust cycle is rerun until the desired coating thickness is attained.

TABLE I

Comparison Of Anodized Substrate Of The Prior Art And The Present Invention Made By Batch And Continuous Processes

|  | Quality* | Consistency* | Quality x Consistency |
|---|---|---|---|
| Prior Art Batch | 3 | 3 | 9 |
| Invention Batch | 4 | 5 | 20 |
| Prior Art Continuous | 3 | 3 | 9 |
| Invention Continuous | 5 | 5 | 25 |

*Quality: 1 = poor, 2 = less than satisfactory, 3 = satisfactory, 4 = more than satisfactory, and 5 = excellent
*Consistency: 1 = poor, 2 = less than satisfactory, 3 = satisfactory, 4 = more than satisfactory, and 5 = excellent A benefit of the present invention in regard to a continuous anodizing system is the ability to produce an anodized substrate having a better quality and consistency from location to location, both linear and areal, over the length and better than an anodized substrate made without a coating thickness monitor of the present invention, and preferably, communicating with a controller. A further benefit of the present invention is the ability to produce an anodized substrate having a better quality and consistency from batch-to-batch, both linear and areal, over the length and surface better than an anodized substrate made without a coating thickness monitor of the present invention, and preferably, communicating with a controller. Table 1 includes a comparison of the quality (e.g., conformity to design specifications), consistency (e.g., the uniformity of a manufactured anodized substrate from location to location and/or batch-to-batch), and quality x consistency for a continuous anodizing system of the present invention and the prior art. Although an anodized substrate of the prior art may be satisfactory, with respect to both quality and consistency, an anodized substrate according to the present invention possesses excellent quality and excellent consistency.

In operation, an anodizing system 10 having a coating thickness monitor 12 provides a means for controlling, validating and documenting process quality. Also, these benefits may be realized economically while improving the overall coating. The anodizing system 10 eliminates the subjectivity in process coating of metal substrates and, preferably, aluminum and aluminum alloys. A coating thickness monitor may be used to eliminate defective coated products from a manufacturing stream. In this way, commercial benefits such as reduced scrap, increased throughput, reduced labor costs, and reduced insurance premiums for product liability may be realized.

Protective coatings are used to prevent oxidation and corrosion of the aluminum and its alloys in numerous applications, such as in the aircraft industry. In many applications, after anodizing, additional coatings (e.g., barrier coating) may be added to promote adhesion of subsequent coatings.

Additional and subsequent coatings are typically of an organic nature, such as epoxies (e.g., epoxy polyamine, epoxy polyamide primer, . . . etc.), polyurethane, resins, composite coating components and top coats (e.g., paint and decals). Typically some type of applicator is used to provide the additional and/or subsequent coatings to the substrate. Non-limiting examples of applicators include coating apparatus such as projection type, spray type, immersion type, substrate-confined pool type, and the like.

In an anodizing system 10, an aluminum substrate is stripped of surface contaminates such as oxidation products, oils (including fingerprints from handling) and waxes. A washing of the surface of the aluminum substrate in a detergent removes oils and waxes. A pickling operation using a chemical enchant removes oxidation products. Cleaning a substrate surface in this way allows an anodizing current to be evenly distributed across the surface of a product to form a uniform coating thickness (e.g., reduce thickness variation). Also, a low electrical resistance exists at the start of the anodizing operation. Anodizing of aluminum is started immediately following substrates washing and pickling to prevent the formation of any parasitic oxidation products. During anodizing, aluminum oxide crystals grow on the surface as current passes through the surface. Following anodizing, further coatings, as discussed above, may be applied to the substrate.

The thickness of an anodized coating and further coating is measured using the coating thickness monitor 12 of the present invention, that in a preferred embodiment operates using interferometry that is independent of substrate thickness. In this way, coating thickness monitor 12 is non-contact, non-destructive, fast, robust and reliable. Also, coating thickness monitor 12 may facilitate simultaneous thickness measurement of an anodized coating and further coating. The use of a guide(s) based on fiber optic technology provides intrinsic isolation of the coating thickness monitor 12 from the process. Also, in situ measurement inside the anodized bath or at strategic inspection points may be simplified.

In a test of the coating thickness monitor 12 of the present invention, the radiation source was coherent white light provided to a coated substrate by a multiple guide optical coupler composed of a plurality of optical fibers. A first guide illuminated the coated substrate surface and a second guide captured and transmitted the reflected light to a detector. One end of the guide system combines the two guides and is coupled to the coated substrate by collating lenses. The opposite end of the guide system diverges to the radiation source of the detector. The composite reflection is transmitted to the detector, which on this embodiment is a spectrometer. The interference within the composite reflection is superimposed onto the reflection signal. Fast Fourier Transformation (FFT) analysis is used to determine the thickness. The parametric set-up allows the coating thickness monitor 12 to be configured to various coating types.

Equipment used in a coating thickness monitor according to the present invention include a spectrometer (Model DSPec/1024/6 having a DSP based spectrometer with an about 1024 element detector available from Analytical Technologies, L.L.C., Morganton N.C.); a radiation source (Model HALXE 50 having a composite halogen/Xenon spectral lamp, with shutter available from Analytical Technologies, L.L.C., Morganton N.C.); a guide system including a plurality of optical fibers (Model 6/1/SMA/FS made from fused silica with 6 detectors around 1 illuminator in SMA terminal, available from Analytical Technologies, L.L.C., Morganton N.C.); and a probe (Model 50/5/SMA including a tube mounted lens with an about 50 mm focal distance, an about 5 mm spot size, SMA terminal, available from Analytical Technologies, L.L.C., Morganton N.C.).

This equipment was interfaced with a personal computer (PC) running a program entitled FTM ProVIS software available from Dipl.-Ing. (FH) Thomas Fuchs, Ingenieurburo fur Angewandte Spektrometrie, Roentgenstr. 33--D--73431 Aalen--Germany.

The interference of two light rays may be described with the following simplified formula:

$$I(1)=A+B*\cos[2p*Dr/1+Dd],$$

where:

I(1) is an interference intensity for wavelength 1;
A contains the intensity of the two light rays;
B is an amplitude of the cosine function;
1 is a wavelength;
Dr is an optical path difference (thickness); and
Dd is a phase shift of the two light rays.

The optical path difference "Dr" itself is the product of the required geometric thickness "d" and the refractive index "n": Dr=2 n (1)*d. Generally, the refractive index "n" is a function of the wavelength "1", which is described as "dispersion" (see below) and in the present case was assumed to be about 1.4789 for alumina.

In the FTM ProVIS software, the required geometric thickness "d" is calculated by the determination of the interference function shown above (the expression "Dr/1" corresponds to a frequency function). This frequency was determined with the help of a "Fast Fourier Transformation" (in shortened form: FFT). In the reciprocal representation of the interference spectrum, the peak position of the Fourier-transformed interference (the Fourier-spectrum, or short: FFT-spectrum), with known dispersion "n(1)", directly supplies the film thickness. The FTM ProVIS software may take into account the dispersion by using a polynomial formula, following the dispersion formula according to Cauchy (dispersion correction):

$$n(1)=n+B/1^2+C/(1^2*1^2),$$

where:

n(1) is the dispersion of a wavelength 1;
n is a polynomial constant;
B and C are polynomial factors; and
1 is a wavelength.

An aluminum 1100 alloy substrate having an anodized coating and a polymer coating was tested using a coating thickness monitor 10 according to the present invention. Scanning electron microscopy (SEM) measurements (viewing area of about 1.5 square micrometers) of coated sample cross sections were used to confirm parametric (set-up) conditions of the coating thickness monitor 10 and illustrate surface topography. An area of interest on an aluminum 1100 alloy substrate was adjustable. An about 3.75 millimeter diameter light spot size produced an about 5.89 square millimeter analyzed area. The measurement speed was set at about 500 measurements per second. The capability of multi-layer analysis was verified by the simultaneous coating thickness measurement of an anodized coating and polymer coating. The coating thickness measurements were independent of substrate thickness and eliminated any need for destructive, time consuming cross-sectioning.

Figure 7:
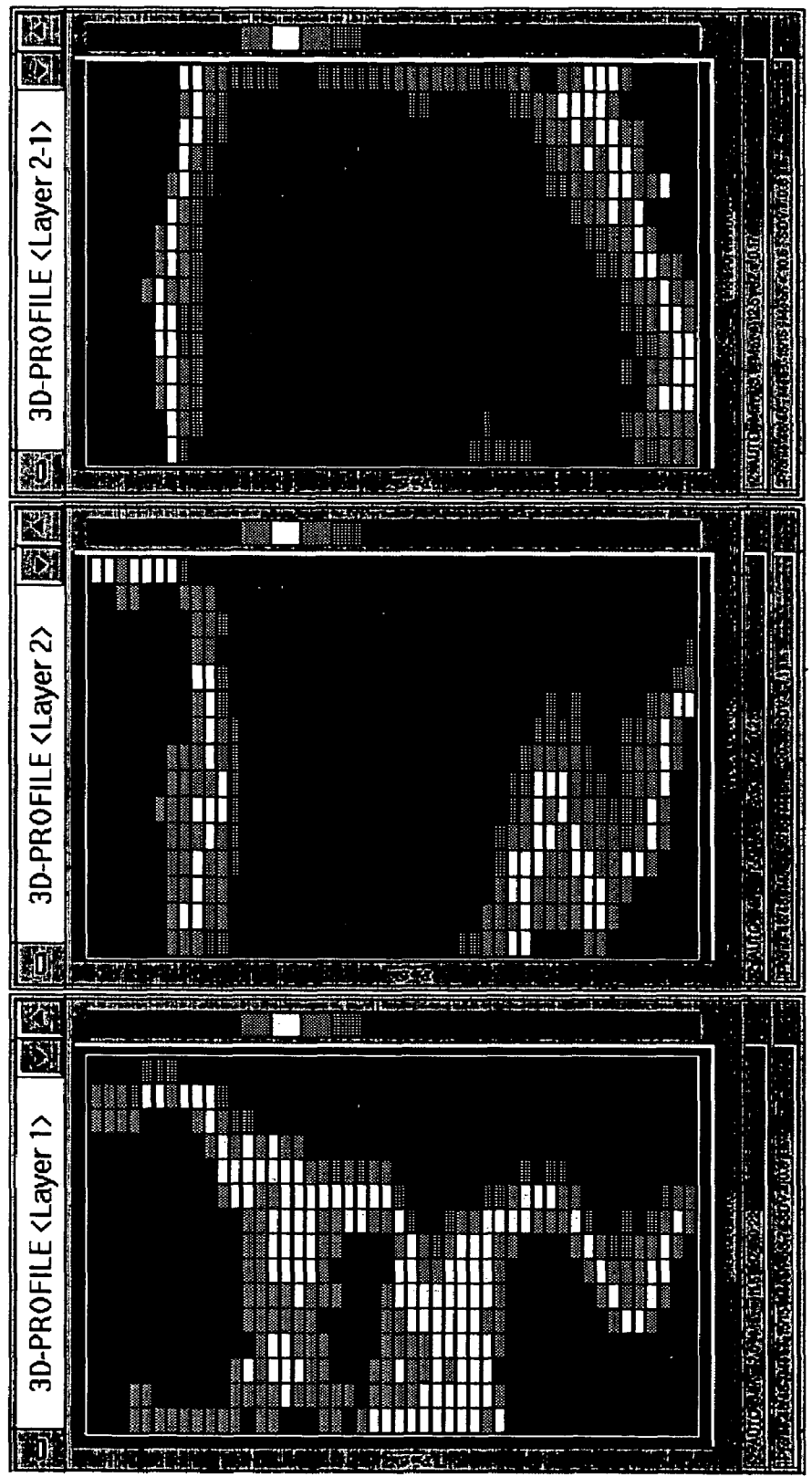
FIG. 7A depicts a topographic thickness profile of a first layer over an area of an anodized aluminum 1100 alloy substrate according to an aspect of the present invention.
FIG. 7B depicts a topographic thickness profile of a second layer over the same area as shown in FIG. 7A of an anodized aluminum 1100 alloy substrate according to an aspect of the present invention.
FIG. 7C depicts a composite topographic thickness profile of the first layer of FIG. 7A and the second layer of FIG. 7B of an anodized aluminum 1100 alloy substrate according to an aspect of the present invention.

Also, it was seen that larger surface areas may be accurately measured. FIG. 7A depicts a topographic thickness profile of a first layer over an area of an anodized aluminum 1100 alloy substrate. FIG. 7B depicts a topographic thickness profile of a second layer over the same area, as shown in FIG. 7A, of the anodized aluminum 1100 alloy substrate. FIG. 7C depicts a composite topographic thickness profile of the first layer of FIG. 7A and the second layer of FIG. 7B of the anodized aluminum 1100 alloy substrate. This data may be used for determining the quality and consistency of the anodized substrate of the present invention. A user of the present invention may set ranges for a first layer and/or a second layer. An algorithm may perform the task of developing a topographic result, and the result may be color-coated for too thick, within specification, and too thin of a coating.

Figure 8:
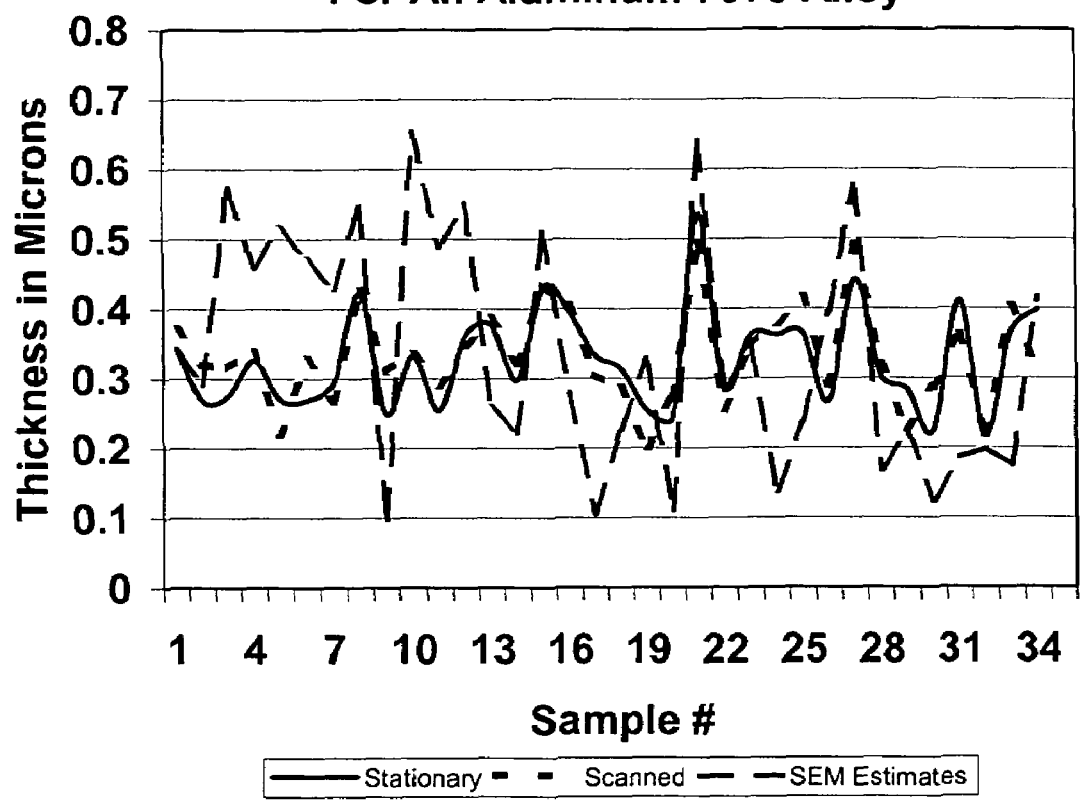
FIG. 8 depicts a comparison of coating thickness determine by fixed measurement, scanned measurement, and measurement made using a scanning electron microscope for an anodized aluminum 7075 alloy substrate according to an aspect of the present invention.
Figure 9:
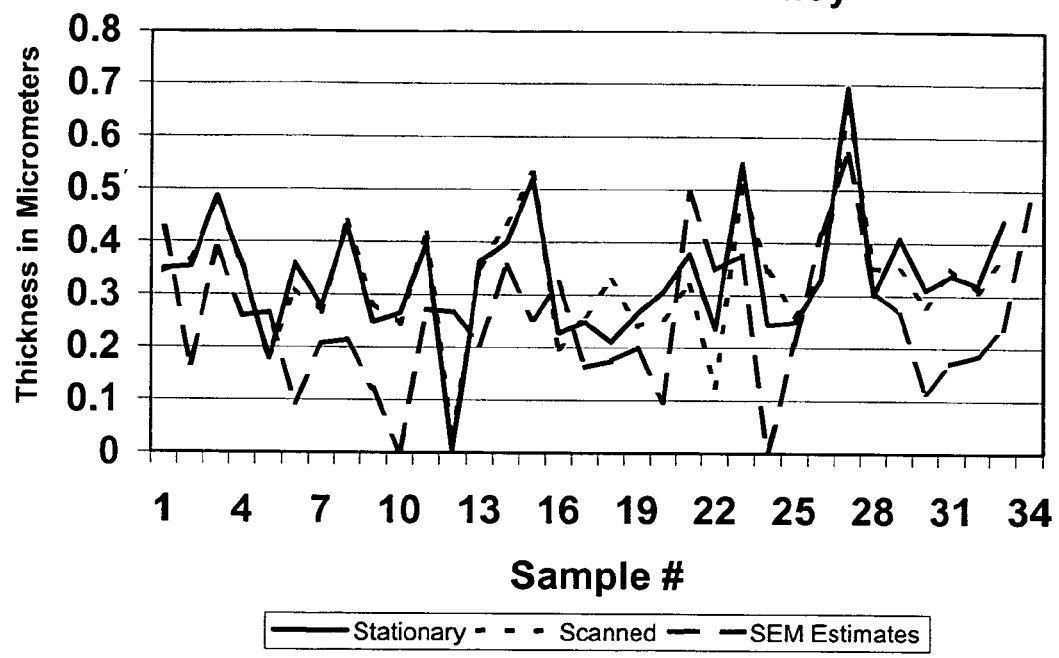
FIG. 9 depicts a comparison of coating thickness determine by fixed measurement, scanned measurement, & measurement made using a scanning electron microscope for an anodized aluminum 2024 alloy substrate according to an aspect of the present invention.

Coating thickness measurements were also made on an aluminum 7075 alloy substrate having an anodized coating and an aluminum 7075 alloy substrate having an anodized coating using a coating thickness monitor 10, according to the present invention. As with the aluminum 1100 alloy substrate, scanning electron microscopy (SEM) measurements were made. Two measurement modes, namely, fixed and scanning, were compared to measurements using an SEM. The measurement interval was about 1 mm for the total scan area. The wavelength range for the FTM ProVIS software was specified from about 450 to about 950 nanometers. About 500 measurements per scan over an about 1 mm scan area were made. FIG. 8 depicts a comparison of coating thickness determined by fixed measurement, scanned measurement, and measurements made using a scanning electron microscope for an anodized aluminum 7075 alloy substrate according to an aspect of the present invention. FIG. 9 depicts a comparison of coating thickness determine by fixed measurement, scanned measurement, and measurements made using a scanning electron microscope for an anodized aluminum 2024 alloy substrate, according to an aspect of the present invention. These results show that the measurement of the coating thickness may be performed by either fixed measurements or scanned measurements. Both measurement techniques correlate well with the measurements made using a SEM while being nondestructive and non-contact.

Protective layers are applied to anodized surfaces in most cases to protect the integrity of the end product. Coating thickness may affect performance quality. Some examples of applications that may include a protective layer applied to anodized surfaces include, without limitation, protective layers applied to an anodized aluminum surface used in transportation vehicles and building materials, medical devices, barrier layers applied to food or beverage packaging containers, protective hard coatings applied to cookware, and polymer layers applied to electronic devices.

The method employs a spectroscopic approach that measures reflected light from the sample. The light reflection contains at least three reflection signals which are returned from (1) the surface, (2) the border or interface of the organic coating and anodized layer, and a signal from the (3) border of the anodization layer and aluminum surface.

The light may be delivered by the apparatus to the surface. A reflection signal is collected and then analyzed by a spectroscopic means using a spectrometer (the apparatus) where it is divided into specific wavelengths of interest. When compared to a bare reference of similar material, the reflectance spectrum may contain multiple interference signals which contain periodic frequencies representative of the layers which interfere due to a change in refraction at each layer's respective border.

This method utilizes the analysis technique employed by the analyzer described above (optIcons® OTC {optical thickness control} from Analytical Technologies, L.L.C., Morganton N.C.)) that employs a self-optimizing setup to facilitate separation of multiple layers from the convoluted interference spectrum. The technique searches the reflectance spectrum for periodic repetitions in intensity which is produced by the interference effect of multiple layers applied to the anodized surface.

Figure 10:
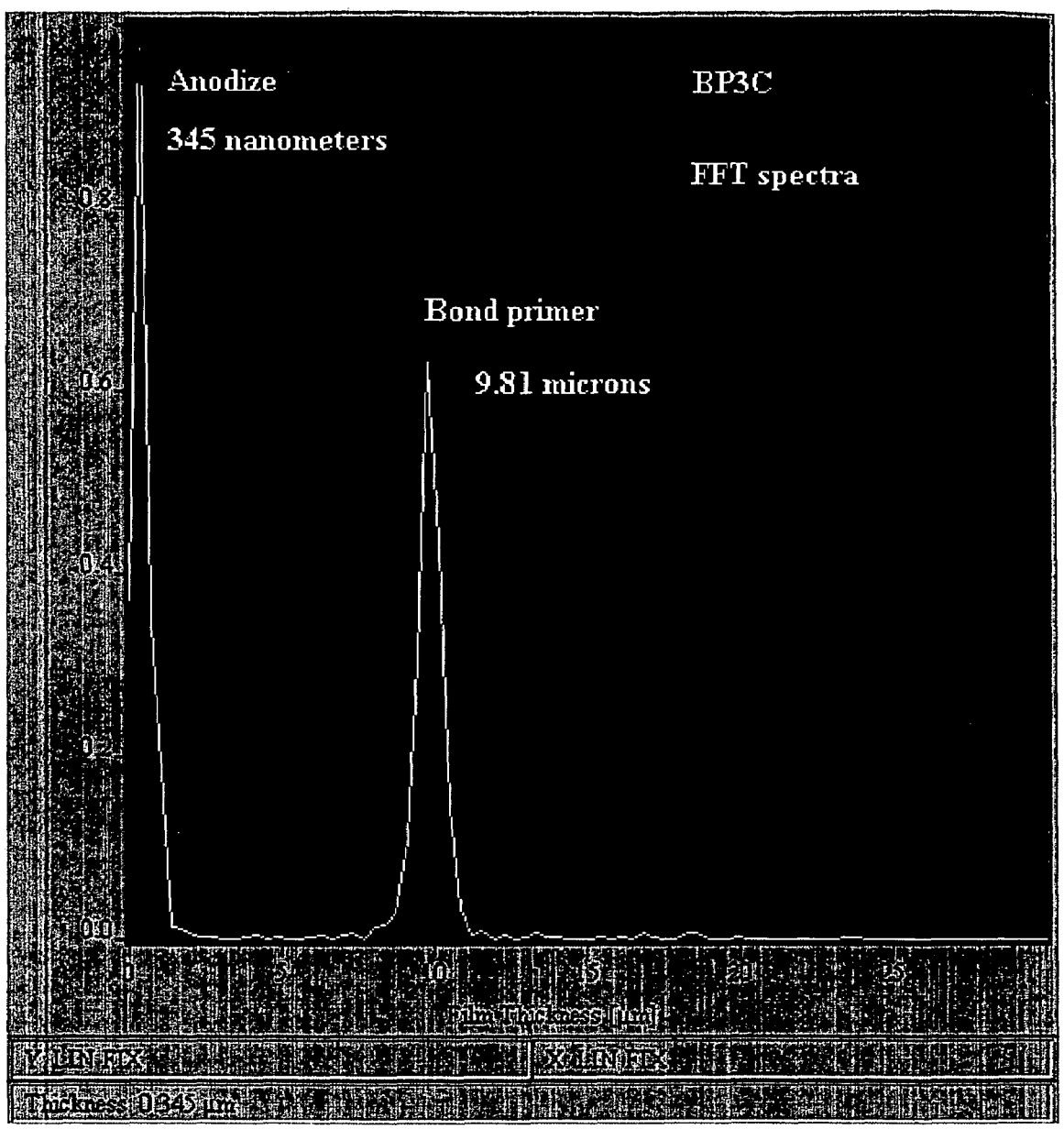
FIG. 10 depicts an FFT analysis comparison of coating thickness.
Figure 11:
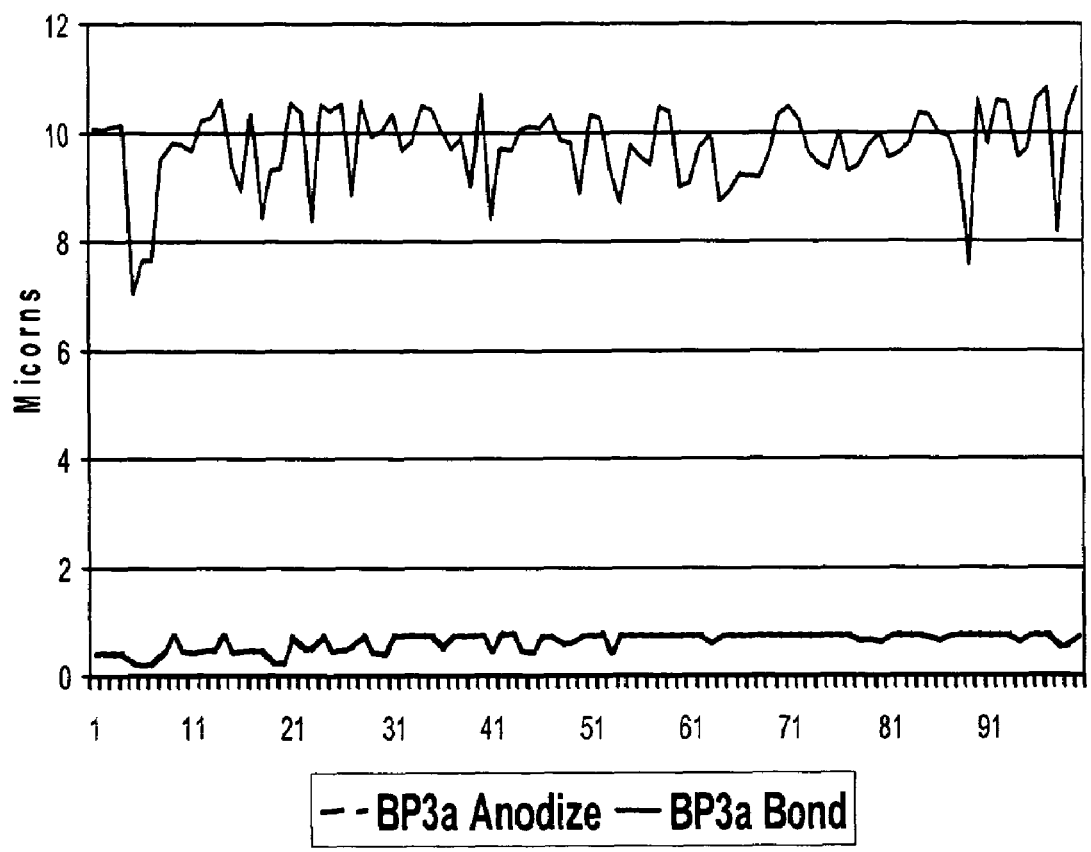
FIG. 11 depicts a two-layer thickness trend plot.

Illustrated as FIG. 10 and FIG. 11 are two charts showing how the optIcons® analyzer is employed to search through the reflected light spectrum. At least two dominant frequencies are found through the use of the FFT analysis technique currently employed. The frequencies are categorized by the optIcons® analyzer. The lower frequency is representative of the anodization layer and higher frequency is representative the bond primer (organic layer) applied to the anodized surface.

The two layer thickness trend plot illustrates the novelty of the measurement and analysis technique and is also used as a process control indicator to illustrate how the layers are measured simultaneously at each point with unsurpassed precision and accuracy.

Certain modifications and improvements will occur to those skilled in the art upon a reading of the foregoing description. By way of example, a real time process to control specified layer thickness for anodizing and a further coating of a substrate may be achieved based upon using an optical interference measurement technique employing monochromatic or polychromatic illumination or detection and an evaluation algorithm for determining thickness based upon FFT. Likewise, a statistical surface evaluation technique for layer thickness profiles using one or more axis of movement over any area of interest, either manually or automated multi-axis positioning system, may be suitable for use in a dip tank, or in an inspection booth. Further, the measurement on multiple surfaces (front, rear, or side) of flat piece goods may be achieved. A measurement mode on curved surfaces of irregular shape could also be achieved.

Also, appropriate measuring points on a parts rack could be achieved. This may be affected by aligning the optical sensors to achieve correct optical throughput and by positioning the measuring probe in various points on a sample part racks. Further, positioning the measuring probe on front, rear, or side of a part may be beneficial. Moreover, finding a statistical variation thickness would be helpful in process control and product quality and consistency. This might be affected by determining average thickness over a desired area of interest; determining the statistical variation in thickness over a desired area of interest; or determining thresholds of acceptability.

It should be understood that all such modifications and improvements have been deleted herein for the sake of conciseness and readability but are properly within the scope of the following claims.

What is claimed is:

1. A coating thickness monitor for measuring the thickness of at least a portion of a coated-anodized coating on at least a portion of a substrate, said coating thickness monitor including:
   (a) at least one radiation source directed at at least a portion of the anodized substrate;
   (b) at least one probe for capturing at least a portion of the radiation reflected and refracted by the anodized coating on the anodized substrate, the captured radiation being at least a portion of the radiation directed at the anodized substrate from said radiation source;
   (c) at least one detector in communication with said at least one probe, said at least one detector capable of processing the captured radiation to allow a determination of at least the thickness of the anodized coating on the substrate; and
   (d) a guide system capable of transmitting the captured radiation from said at least one probe to said at least one detector.

2. The coating thickness monitor according to claim 1 wherein said guide system is an optical guide.

3. The coating thickness monitor according to claim 2 wherein said optical guide is an optical fiber.

4. The coating thickness monitor according to claim 1 wherein said processing the captured radiation to allow a determination of at least the thickness of the anodized coating on the substrate by said coating thickness monitor includes at least one of using a color, using an interference pattern, using an amount of absorbed radiation, using an intensities ratio of a minimum reflected radiation wavelength and a maximum reflected radiation wavelength, and using a Fast Fourier Transformation (FFT) of the captured radiation.

5. The coating thickness monitor according to claim 1 wherein said processing the captured radiation to allow a determination of at least the thickness of the anodized coating on the substrate by said coating thickness monitor includes using a Fast Fourier Transformation (FFT) of the captured radiation.

6. The coating thickness monitor according to claim 1 wherein said at least one radiation source comprises polychromatic radiation.

7. The coating thickness monitor according to claim 6 wherein said polychromatic radiation is one or more of ultraviolet, visible, or infrared radiation.

8. The coating thickness monitor according to claim 1 wherein said at least one detector comprises one or more of an interferometer, photoelectric receiver array, CCD element, or an optoelectric transducer.

9. The coating thickness monitor according to claim 1 wherein the guide system is coupled with the radiation source to direct radiation to the surface of the substrate.

10. The coating thickness monitor according to claim 1, further comprising a computer.

11. The coating thickness monitor according to claim 1, further comprising an additional source of radiation.

12. A method for measuring coating thickness of at least a portion of a coated-anodized coating on at least a portion of a substrate wherein said coated-anodized coating comprises a barrier coating, said method including:
    (a) providing a coating thickness monitor;
    (b) directing at least one radiation source at at least a portion of the coated-anodized substrate;
    (c) capturing, using at least one probe, at least a portion of the radiation reflected and refracted by the coated-anodized coating on the substrate, the captured radiation being at least a portion of the radiation directed the coated-anodized substrate from said radiation source;
    (d) transmitting the captured radiation using a guide system from said at least one probe to at least one detector; and
    (e) processing the captured radiation to allow a determination of at least the thickness of the anodized coating on the substrate.

13. The method according to claim 12 for measuring coating thickness of at least a portion of a coated-anodized coating wherein said barrier coating comprises an organic coating.

14. The method according to claim 13 for measuring coating thickness of at least a portion of a coated-anodized coating wherein said organic coating comprises at least one of an epoxy and a polyurethane.

15. The method according to claim 14 for measuring coating thickness of at least a portion of a coated-anodized coating wherein said epoxy coating comprises at least one of an epoxy polyamine and a epoxy polyamide primer.

16. The method according to claim 13 for measuring coating thickness of at least a portion of a coated-anodized coating wherein said organic coating comprises a resin.

17. The method according to claim 13 for measuring coating thickness of at least a portion of a coated-anodized coating wherein said organic coating comprises a composite coating.

18. The method according to claim 13 for measuring coating thickness of at least a portion of a coated-anodized coating wherein said organic coating comprises a top coat.

19. The method of claim 12, further comprising displaying the determination of at least the thickness of the anodized coating on the substrate on a computer monitor.

* * * * *